US006369088B2

(12) United States Patent
Schoenafinger et al.

(10) Patent No.: US 6,369,088 B2
(45) Date of Patent: Apr. 9, 2002

(54) SUBSTITUTED 3-PHENYL-5-ALKOXY-1,3,4-OXADIAZOL-2-ONES, THEIR PREPARATION AND THEIR USE AS PHARMACEUTICALS

(75) Inventors: Karl Schoenafinger, Alzenau; Stefan Petry, Frankfurt; Guenter Mueller, Sulzbach; Karl-Heinz Baringhaus, Wölfersheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/799,082

(22) Filed: Mar. 6, 2001

(30) Foreign Application Priority Data

Mar. 7, 2000 (DE) .......................... 100 10 968
Jan. 18, 2001 (DE) .......................... 101 02 265

(51) Int. Cl.[7] .................. C07D 271/113; A61K 31/4245
(52) U.S. Cl. ...................................... 514/364; 548/144
(58) Field of Search ........................... 548/144; 514/364

(56) References Cited

U.S. PATENT DOCUMENTS

| 4,076,824 A | 2/1978 | Boesch |
| 4,150,142 A | 4/1979 | Boesch |
| 5,093,343 A | 3/1992 | Bonse et al. |
| 5,236,939 A | 8/1993 | Bonse et al. |

FOREIGN PATENT DOCUMENTS

| DE | 26 03 877 C2 | 8/1976 |
| DE | 26 04 110 A | 8/1976 |
| EP | 0 048 040 B1 | 3/1982 |
| EP | 0 067 471 B1 | 12/1982 |
| EP | 0 419 918 A2 | 4/1991 |
| WO | WO 96/13264 | 5/1996 |

OTHER PUBLICATIONS

Nilsson, S. and P. Belfrage, "Purification of Hormone–Sensitive Lipase by High–Performance Ion Exchange Chromatography," Analytical Biochemistry, 158, 399–407 (1986).
Fredrikson, G. et al., "Hormone–sensitive Lipase of Rat Adipose Tissue," The Journal of Biological Chemistry, 256, No. 12, pp. 6311–6320 (Jun. 25, 1981).
Tornqvist, H. and P. Belfrage, "Purification and Some Properties of a Monoacylglycerol–Hydrolyzing Enzyme of Rat Adipose Tissue," The Journal of Biological Chemistry, 251, No. 3, pp. 813–819 (Feb. 10, 1976).
Abstract for German Patent DE 26 04 110 A, Boesch, R., "Oxadiazolinone Derivatives as Anthelmintics—from Suitable Carbazate Compounds and phosgene Followed by Cyclisation," Derwent WPI Database.
Abstract for German Patent DE 26 03 877 C2, Boesch, R., "Alkoxy–substituted Oxadiazolin–2–one Derivatives—e.g. 5–Methoxy–3–(2–methoxyphenyl)–1,3,4,–oxadiazolin–2–one," Derwent WPI Database.
Abstract for German Patent DE 0 419 918 A2, Bonse, G., et al., "Substituted 1,3,4–oxa (or thia)–diazolinone Derivatives—Used in Treatment of Endoparasitic Infections Caused by Cesodes, Trematodes, Nematodes and Acanthocephalus," Derwent WPI Database.

Primary Examiner—Robert Gerstl
(74) Attorney, Agent, or Firm—Finnegan, Henderson, Farabow, Garrett, & Dunner L.L.P.

(57) ABSTRACT

Substituted 3-phenyl-5-alkoxy-1,3,4-oxadiazol-2-ones of the formula 1 are described,

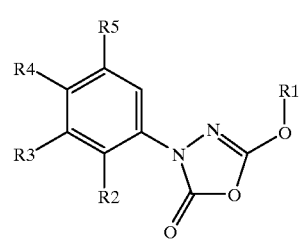

in which $R^1$ is substituted $C_1$–$C_6$-alkyl and $C_3$–$C_9$-cycloalkyl, $R^2$, $R^3$, $R^4$ and $R^5$ are hydrogen, halogen, nitro, $C_1$–$C_4$-alkyl, $C_1$–$C_9$-alkyloxy, substituted $C_6$–$C_{10}$-aryl-$C_1$–$C_4$-alkyloxy, $C_6$–$C_{10}$-aryloxy, $C_6$–$C_{10}$-aryl, $C_3$–$C_8$-cycloalkyl or O—$C_3$—$C_8$-cycloalkyl, or 2-oxopyrrolidin-1-yl, 2,5-dimethylpyrrol-1-yl or $NR^6$-A-$R^7$, with the proviso that $R^2$, $R^3$, $R^4$ and $R^5$ are not simultaneously hydrogen, and at least one of the radicals $R^2$, $R^3$, $R^4$ or $R^5$ is the radical 2-oxopyrrolidin-1-yl, 2,5-dimethylpyrrol-1-yl or $NR^6$-A-$R^7$, wherein $R^6$=hydrogen, $C_1$–$C_4$-alkyl or substituted $C_6$–$C_{10}$-aryl-$C_1$–$C_4$-alkyl, A=a single bond, $CO_n$, $SO_n$ or CONH, n=1 or 2, $R^7$=hydrogen, substituted $C_1$–$C_{18}$-alkyl, $C_2$–$C_{18}$-alkenyl, $C_6$–$C_{10}$-aryl-$C_1$–$C_4$-alkyl, $C_5$–$C_8$-cycloalkyl-$C_1$–$C_4$-alkyl, $C_5$–$C_8$-cycloalkyl, $C_6$–$C_{10}$-aryl-$C_2$–$C_6$-alkenyl, $C_6$–$C_{10}$-aryl, biphenylyl, biphenylyl-$C_1$–$C_4$-alkyl, indanyl, or the group Het-$(CH_2)_r$—, wherein r=0, 1, 2 or 3 and Het=a saturated or unsaturated 5-7-membered heterocycle, which may be optionally benzo-fused and optionally substituted, and proceses for their preparation. The compounds of formula 1 show an inhibitory effect on hormone-sensitive lipase, HSL.

41 Claims, No Drawings

SUBSTITUTED 3-PHENYL-5-ALKOXY-1,3,4-OXADIAZOL-2-ONES, THEIR PREPARATION AND THEIR USE AS PHARMACEUTICALS

This invention relates to substituted 3-phenyl-5-alkoxy-1,3,4-oxadiazol-2-ones, which show an inhibitory effect on hormone-sensitive lipase (HSL), and their pharmaceutically acceptable salts or acid addition salts. The present invention further relates to processes for the preparation of 3-phenyl-5-alkoxy-1,3,4-oxadiazol-2-ones, to the use of 3-phenyl-5-alkoxy-1,3,4-oxadiazol-2-ones and their pharmaceutically acceptable salts or acid addition salts as pharmaceuticals, including their use as inhibitors of HSL, and to pharmaceutical compositions comprising 3-phenyl-5-alkoxy-1,3,4-oxadiazol-2-ones and their pharmaceutically acceptable salts or acid addition salts, including their use in the treatment of non-insulin dependent diabetes mellitus and diabetic syndrome.

Certain 5-alkoxy-1,3,4-oxadiazol-2-ones substituted with an ortho-substituted phenyl ring or with fused-on five- or six-membered rings have anthelmintic (DE-A 26 04 110) and insecticidal effects (DE-A 26 03 877, EP-B 0 048 040, EP-B 0 067 471).

Certain 5-phenoxy-1,3,4-oxadiazol-2-ones with an ortho-substituted phenyl ring as substituents show an endoparasiticidal effect (EP-A 0 419 918).

An aim of the invention was to find compounds which show an inhibitory effect on hormone-sensitive lipase, HSL.

The present invention relates to substituted 3-phenyl-5-alkoxy-1,3,4-oxadiazol-2-ones of the formula 1:

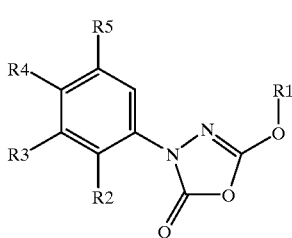

(1)

in which:

R$^1$ is C$_1$–C$_6$-alkyl, C$_3$–C$_9$-cycloalkyl, wherein both groups are optionally substituted one or more times by phenyl, C$_1$–C$_4$-alkyloxy, S—C$_1$—C$_4$-alkyl, N(C$_1$–C$_4$-alkyl)$_2$, and wherein phenyl is optionally substituted one or more times by halogen, C$_1$–C$_4$-alkyl, C$_1$–C$_4$-alkyloxy, nitro, CF$_3$; and R$^2$, R$^3$, R$^4$ and R$^5$ independently of one another are hydrogen, halogen, nitro, C$_1$–C$_4$-alkyl, C$_1$–C$_9$-alkyloxy; C$_6$–C$_{10}$-aryl-C$_1$–C$_4$-alkyloxy, C$_6$–C$_{10}$-aryloxy, C$_6$–C$_{10}$-aryl, C$_3$–C$_8$-cycloalkyl or O—C$_3$–C$_8$-cycloalkyl, each of which is optionally substituted once, twice or three times by halogen, CF$_3$, C$_1$–C$_4$-alkyloxy or C$_1$–C$_4$-alkyl; 2-oxopyrrolidin-1-yl, 2,5-dimethylpyrrol-1-yl or NR$^6$-A-R$^7$, with the proviso that R$^2$, R$^3$, R$^4$ and R$^5$ are not simultaneously hydrogen, and at least one of the radicals R$^2$, R$^3$, R$^4$ or R$^5$ is the radical 2-oxopyrrolidin-1-yl, 2,5-dimethylpyrrol-1-yl, or NR$^6$-A-R$^7$, and wherein:

R$^6$ is hydrogen, C$_1$–C$_4$-alkyl or C$_6$–C$_{10}$-aryl-C$_1$–C$_4$-alkyl, wherein aryl may be substituted by halogen, CF$_3$, C$_1$–C$_8$-alkyloxy or C$_1$–C$_4$-alkyl;

A is a single bond, CO$_n$, SO$_n$, or CONH;

n is 1 or 2;

R$^7$ is hydrogen, C$_1$–C$_{18}$-alkyl or C$_2$–C$_{18}$-alkenyl, wherein C$_1$–C$_{18}$-alkyl or C$_2$–C$_{18}$alkenyl are optionally substituted one to three times by C$_1$–C$_4$-alkyl, halogen, CF$_3$, C$_1$–C$_4$-alkyloxy, N(C$_1$–C$_4$-alkyl)$_2$, —COOH, C$_1$–C$_4$-alkyloxycarbonyl, C$_6$–C$_{12}$-aryl, C$_6$–C$_{12}$-aryloxy, C$_6$–C$_{12}$-arylcarbonyl, C$_6$–C$_{10}$-aryl-C$_1$–C$_4$-alkyloxy or oxo, wherein aryl is in turn optionally substituted by halogen, C$_1$–C$_4$-alkyl, aminosulfonyl or methylmercapto;

C$_6$–C$_{10}$-aryl-C$_1$–C$_4$-alkyl, C$_5$–C$_8$-cycloalkyl-C$_1$–C$_4$-alkyl, C$_5$–C$_8$-cycloalkyl, C$_6$–C$_{10}$-aryl-C$_2$–C$_6$-alkenyl, C$_6$–C$_{10}$-aryl, biphenylyl, biphenylyl-C$_1$–C$_4$-alkyl, indanyl, each of which is optionally substituted once or twice by C$_1$–C$_{18}$-alkyl, C$_1$–C$_{18}$-alkyloxy, C$_3$–C$_8$-cycloalkyl, COOH, hydroxyl, C$_1$–C$_4$-alkylcarbonyl, C$_6$–C$_{10}$-aryl-C$_1$–C$_4$-alkyl, C$_6$–C$_{10}$-aryl-C$_1$–C$_4$-alkyloxy, C$_6$–C$_{10}$-aryloxy, nitro, cyano, C$_6$–C$_{10}$-aryl, fluorosulfonyl, C$_1$–C$_6$-alkyloxycarbonyl, C$_6$–C$_{10}$-arylsulfonyloxy, pyridyl, NHSO$_2$–C$_6$–C$_{10}$-aryl, halogen, CF$_3$ or OCF$_3$, wherein alkyl is in turn optionally substituted by C$_1$–C$_4$-alkyloxycarbonyl, CF$_3$ or carboxyl, and aryl is also optionally substituted by halogen, CF$_3$ or C$_1$–C$_4$-alkyloxy;

or the group Het-(CH$_2$)$_r$—, wherein r=0, 1, 2 or 3 and Het=a saturated or unsaturated 5–7-membered heterocycle, optionally benzo-fused and optionally substituted by C$_1$–C$_4$-alkyl, C$_6$–C$_{10}$-aryl, halogen, C$_1$–C$_4$-alkyloxy, C$_1$–C$_4$-alkyloxycarbonyl, C$_6$–C$_{10}$-aryl-C$_1$–C$_4$-alkyl, C$_6$–C$_{10}$-aryl-C$_1$–C$_4$-alkylmercapto or nitro, wherein the benzo-fused aryl is in turn optionally substituted by halogen, C$_1$–C$_4$-alkyloxy or CF$_3$ and the alkyl in arylalkyl is also optionally by methoxy and CF$_3$, and their pharmaceutically acceptable salts and acid addition salts.

Said aryl radicals are optionally substituted one or more times by C$_1$–C$_9$-alkyl, C$_1$–C$_8$-alkyloxy, halogen, and trifluoromethyl. Said cycloalkyl radicals are optionally substituted one or more times by C$_1$–C$_4$-alkyl, C$_6$–C$_{10}$-aryl, and said alkyl radicals are optionally substituted by hydroxyl, di-C$_1$–C$_4$-alkylamino and fluorine. Halogen is fluorine, chlorine, bromine, generally fluorine and chlorine. Alkyl, alkenyl, alkyloxy, etc. are branched or unbranched. The phrase "is optionally substituted" means that the relevant group is or is not substituted.

Pharmaceutically acceptable salts of compounds of the formula 1 include their organic and inorganic salts, as described in Remington's Pharmaceutical Sciences (A. R. Gennard Editor, Mack Publishing Co., Easton, Pa., USA, 17$^{th}$ Ed., p 1418, (1985)). Examples of acidic groups include, inter alia, sodium, potassium, calcium and ammonium salts. Examples of basic groups include, inter alia, salts of hydrochloric acid, sulfuric acid, phosphoric acid, or of carboxylic acids or sulfonic acids, such as, for example, acetic acid, citric acid, benzoic acid, maleic acid, fumaric acid, tartaric acid and p-toluenesulfonic acid.

Typical compounds of the formula 1 are those in which:
R$^1$ is C$_1$–C$_4$-alkyl; and/or
R$^5$ is hydrogen; and/or
R$^2$ is hydrogen, halogen, C$_1$–C$_4$-alkyl, C$_1$–C$_9$-alkyloxy or amino.

Further examples of compounds of the formula 1 are those in which:
R$^3$ is hydrogen, C$_1$–C$_4$-alkyl, C$_6$–C$_{10}$-aryl-C$_1$–C$_4$-alkyloxy, which is optionally substituted in the aryl moiety by halogen, or is NR$^6$-A-R$^7$ wherein $R^6$=hydrogen or benzyl, A=single bond and $R^7$=$C_6$–$C_{10}$-aryl-$C_1$–$C_4$-alkyl, which is optionally substituted by halogen, $CF_3$, cyano, phenyl-$C_1$–$C_4$-alkyloxy, $CF_3$-phenoxy, $C_5$–$C_8$-cycloalkyl or fluorosulfonyloxy;

$C_1$–$C_{12}$-alkyl, which is optionally substituted by $C_1$–$C_4$-alkyloxy, phenyl, $CF_3$ or phenyl-$C_1$–$C_4$-alkyloxy; $C_2$–$C_{12}$-alkenyl;

or the group Het-$(CH_2)_r$—, wherein r=0 or 1, and Het=a saturated or unsaturated 5–7-membered heterocycle, which is optionally benzo-fused and optionally substituted by $C_1$–$C_4$-alkyl or halogen.

Additional compounds of the formula 1 are those in which:

$R^4$ is hydrogen, 2-oxopyrrolidin-1-yl, 2,5-dimethylpyrrol-1-yl or $C_6$–$C_{10}$-aryl-$C_1$–$C_4$-alkyloxy, which is optionally substituted by halogen, and/or: compounds of the formula 1 in which: $R^4$ is $NR^6$-A-$R^7$, wherein $R^6$=hydrogen or methyl, A=single bond and $R^7$=hydrogen;

$C_1$–$C_{12}$-alky, which is optionally substituted once or twice by halogen;

$C_2$–$C_{18}$-alkenyl, which is optionally substituted once or twice by $C_1$-$C_4$-alkyl or $C_1$–$C_4$-alkyloxycarbonyl;

$C_6$–$C_{10}$-aryl-$C_1$–$C_4$-alky, which is optionally substituted by halogen, $C_1$–$C_6$-alkyloxy, $CF_3$, cyano, $C_5$–$C_6$-cycloalkyl, $C_1$–$C_4$-alkyloxycarbonyl, $C_6$–$C_{10}$-aryl-$C_1$–$C_4$-alkyl, $C_6$–$C_{10}$-aryl-$C_1$–$C_4$-alkyloxy, wherein aryl is further optionally substituted by halogen or $CF_3$;

$C_5$–$C_8$-cycloalkyl-$C_1$–$C_4$-alkyl;

or the group Het-$(CH_2)_r$—, wherein r=1, 2 or 3 and Het=a saturated or unsaturated 5–7-membered heterocycle, which is optionally substituted by halogen, $C_1$–$C_4$-alkyloxy or $C_1$–$C_4$-alkyloxycarbonyl, and/or compounds of the formula 1 in which:

$R^4$ is $NR^6$-A-$R^7$, wherein $R^6$=hydrogen,

A=—CO— and $R^7$=$C_1$–$C_{18}$-alkyl, which is optionally substituted by halogen, phenyl, phenoxy, phenylcarbonyl or $C_1$–$C_4$-alkyloxycarbonyl, wherein phenoxy is optionally substituted by methyl, halogen or methylmercapto;

$C_2$–$C_{18}$-alkenyl, which is optionally substituted by $C_6$–$C_{10}$-aryl;

$C_6$–$C_{10}$-aryl, which is optionally substituted by halogen, $C_1$–$C_8$-alkyl, phenyl-$C_1$–$C_4$-alkyl, $CF_3$, $OCF_3$, fluorosulfonyl, $C_1$–$C_4$-alkyloxycarbonyl, phenoxy, wherein aryl is optionally substituted by $C_1$–$C_4$-alkyloxy;

$C_6$–$C_{10}$-aryl-$C_1$–$C_4$-alkyl, wherein alkyl is optionally substituted by methoxy or $CF_3$ and aryl by halogen;

or the group Het-$(CH_2)_r$—, wherein r=0 and Het=a saturated or unsaturated 5–7-membered heterocycle, which is optionally benzo-fused and optionally substituted by $C_1$–$C_4$-alkyl, halogen, $C_1$–$C_4$-alkyloxy, halophenyl or halobenzylmercapto, wherein benzo-fused aryl is optionally substituted by halogen or methoxy, and/or compounds of the formula 1 in which:

$R^4$ is $NR^6$-A-$R^7$, wherein $R^6$=hydrogen,

A=—$CO_2$— and $R^7$=$C_1$–$C_{18}$-alkyl, which is substituted by $CF_3$ or phenyl;

$C_6$–$C_{10}$-aryl;

$C_6$–$C_{10}$-aryl-$C_1$–$C_4$-alkyl, which is substituted by $C_1$–$C_4$-alkyl, halogen, $CF_3$ or $OCF_3$, benzyloxy or phenyl;

or the group Het-$(CH_2)_r$—, wherein r=0 or 1 and Het=a saturated or unsaturated 5–7-membered heterocycle, which is optionally benzo-fused and optionally substituted by $C_1$–$C_4$-alkyl or benzyl, and/or compounds of the formula 1 in which:

$R^4$ is $NR^6$-A-$R^7$, wherein $R^6$=hydrogen,

A=—$SO_2$— and $R^7$=$C_1$–$C_6$-alky, which is optionally substituted by $CF_3$;

$C_2$–$C_4$-alkenyl, which is optionally substituted by phenyl;

$C_6$–$C_{10}$-aryl, which is optionally substituted by $C_1$–$C_6$-alkyl, halogen, $C_1$–$C_4$-alkyloxy or benzyl;

biphenylyl-$C_1$–$C_4$-alkyl substituted by halogen;

or the group Het-$(CH_2)_r$—, wherein r=0 and Het=a saturated or unsaturated 5–7-membered heterocycle, and/or compounds of the formula 1 in which:

$R^4$ is $NR^6$-A-$R^7$, wherein $R^6$=hydrogen,

A=—CO—NH— and $R^7$=$C_1$–$C_{10}$-alkyl, which is optionally substituted by $C_1$–$C_4$-alkyloxycarbonyl, N($C_1$–$C_4$-alkyl)$_2$ or phenyl, which is in turn optionally substituted by halogen or aminosulfonyl;

$C_6$–$C_{10}$-aryl, which is optionally substituted by $C_1$–$C_6$-alkyl, $C_1$–$C_6$-alkyloxy, $C_1$–$C_6$-alkyloxycarbonyl, phenoxy, $OCF_3$, benzyl or pyridyl, wherein alkyl is optionally substituted by $C_1$–$C_4$-alkyloxycarbonyl or carboxyl;

$C_5$–$C_8$-cycloalky, which is optionally substituted by hydroxyl, or indanyl;

or the group Het-$(CH2)^r$—, wherein r=0 or 1 and Het=a saturated or unsaturated 5–7-membered heterocycle, which is optionally substituted by benzyl.

Other typical compounds of the formula 1 are those in which $R^1$ is methyl.

Representative compounds of the formula 1 are those mentioned in Examples 21, 22, 27, 28, 30 to 34, 36 to 42, 53, 54, 58, 60, 62, 65, 69, 71, 74, 92, 97,107,116,128, 130, 136,139,142,152,166 and 171.

The compounds of the invention have a surprising inhibitory effect on hormone-sensitive lipase, HSL, an allosteric enzyme in adipocytes, which is inhibited by insulin and is responsible for the breakdown of fats in fat cells and for the transfer of fat constituents into the blood stream. Inhibition of this enzyme thus corresponds to an insulin-like effect of the compounds of the invention, which eventually leads to a reduction of free fatty acids in the blood and of blood glucose. Therefore, the compounds of the invention can be employed in the treatment of metabolic disturbances such as, for example, non-insulin-dependent diabetes mellitus, diabetic syndrome, and direct damage to the pancreas.

The compounds of the invention can be prepared in various ways by methods known per se.

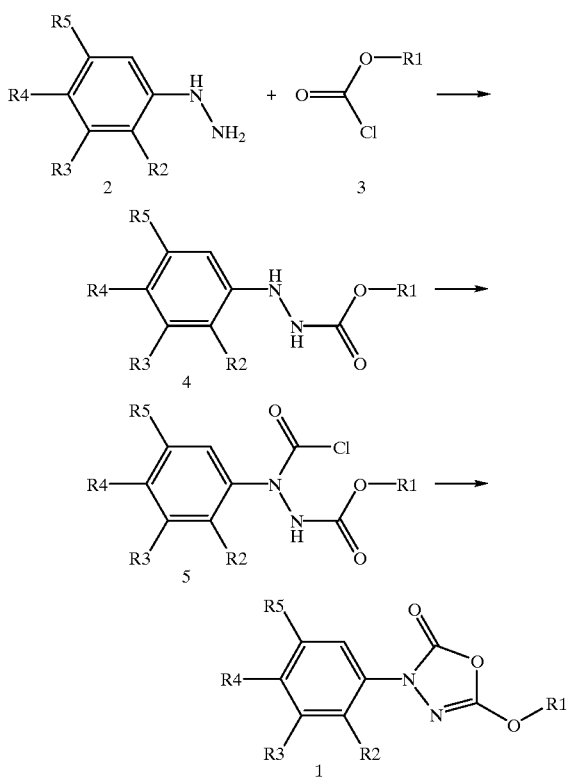

For example, substituted 3-phenyl-5-alkoxy-1,3,4-oxadiazol-2-ones of the formula 1 can be prepared by reacting hydrazines of the formula 2 with chloroformic esters of the formula 3 or other reactive carbonic ester derivatives, in which $R^1$, $R^2$, $R^3$, $R^4$ and $R^5$ are as defined above, to give the compounds of the formula 4, which are acylated with phosgene, carbonyldiimidazole, diphosgene or triphosgene, cyclized and converted, where appropriate, by further chemical modification of the radicals $R^2$–$R^5$, such as, for example, by reduction of nitro to amino radicals by known processes, and subsequent acylation or alkylation, into compounds of the formula 1. Since acids are usually liberated in these reactions, neutralization is advisable by adding bases such as pyridine, triethylamine, sodium hydroxide solution or alkali metal carbonates. The reactions can be carried out in wide temperature ranges. It has proved advantageous to operate in the temperature range from 0° C. to the boiling point of the solvent used. Examples of solvents employed are methylene chloride, THF, DMF, toluene, ethyl acetate, n-heptane, dioxane, and diethyl ether.

The hydrazines of the formula 2 can be prepared by known methods, for example by diazotization of the corresponding anilines and

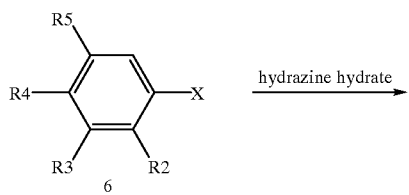

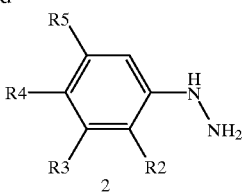

subsequent reduction by known methods or by nucleophilic substitution of suitably substituted phenyl derivatives of the formula 6 (X=F, Cl, Br, I, $OSO_2CF_3$) with hydrazine hydrate. Such suitable phenyl derivatives may be nitro-substituted halobenzenes, such as fluoro- and chloronitrobenzenes, from which the compounds of the invention can be prepared by known methods at a suitable point in the synthetic route by reduction and reaction with acylating or alkylating agents such as, for example, acid chlorides, anhydrides, isocyanates, chloroformic esters, sulfonyl chlorides or alkyl and arylalkyl halides, or by reductive alkylation with aldehydes.

The effect of the compounds of the invention on HSL was tested using the following enzyme assay system:

Enzyme Preparation:

Preparation of Partially Purified HSL:

Isolated rat fat cells were obtained from epididymal adipose tissue from untreated male rats (Wistar, 220–250 g) by collagenase treatment according to published methods (e.g., S. Nilsson et al., Anal. Biochem. 158:399–407 (1986); G. Fredrikson et al., J. Biol. Chem. 256:6311–6320 (1981); H. Tornquist et al., J. Biol. Chem. 251:813–819 (1976)). The fat cells from 10 rats were washed three times by flotation with 50 ml each time of homogenization buffer (25 ml tris/HCl, pH 7.4, 0.25 M sucrose, 1 mM EDTA, 1 mM DTT, 10 μg/ml leupeptin, 10 μg/ml antipain, 20 μg/ml pepstatin) and finally taken up in 10 ml of homogenization buffer. The fat cells were homogenized in a Teflon-in-glass homogenizer (Braun-Melsungen) by 10 strokes at 1500 rpm and 15° C. The homogenate was centrifuged (Sorvall SM24 tubes, 5000 rpm, 10 min, 4° C.). The subnatant between the fatty layer at the top and the pellet was removed and the centrifugation was repeated. The subnatant resulting therefrom was recentrifuged (Sorvall SM24 tubes, 20000 rpm, 45 min, 4° C.). The subnatant was removed and mixed with 1 g of heparin-Sepharose (Pharmacia-Biotech, CL-6B, 5×washed with 25 mM tris/HCl, pH 7.4,150 mM NaCl). After the mixture had been incubated at 4° C. for 60 min (shaking at 15-min intervals), it was centrifuged (Sorvall SM24 tubes, 3000 rpm, 10 min, 4° C.). The supernatant was adjusted to pH 5.2 by adding glacial acetic acid and incubated at 4° C. for 30 min. The precipitates were collected by centrifugation (Sorvall SS34, 12000 rpm, 10 min, 4° C.) and suspended in 2.5 ml of 20 mM tris/HCl, pH 7.0,1 mM EDTA, 65 mM NaCl, 13% sucrose, 1 mM DTT, 10 μg/ml leupeptin/pepstatin/antipain. The suspension was dialyzed against 25 mM tris/HCl, pH 7.4, 50% glycerol, 1 mM DTT, 10 μg/ml leupeptin, pepstatin, antipain at 4° C. overnight and then loaded onto a hydroxy apatite column (0.1 g per 1 ml of suspension, equilibrated with 10 mM potassium phosphate, pH 7.0, 30% glycerol, 1 mM DTT). The column was washed with four volumes of equilibration buffer at a flow rate of 20 to 30 ml/h. The HSL was eluted with one volume of equilibration buffer containing 0.5 M potassium phosphate, and then dialyzed (see above) and concentrated 5- to 10-fold by ultrafiltration (Amicon Diaflo PM 10 filter) at 4° C. The partially purified HSL can be stored at −70° C. for 4 to 6 weeks.

Assay:

To prepare the substrate, 25–50 μCi of [³H] trioleoylglycerol (in toluene), 6.8 μmol of unlabeled trioleoylglycerol and 0.6 mg of phospholipids (phosphatidylcholine/phosphatidylinositol 3:1 w/v) were mixed, dried with $N_2$ and then taken up in 2 ml of 0.1 M $KP_i$ (pH 7.0) by ultrasonic treatment (Branson 250, microtip, setting 1–2, 2×1 min at 1-min intervals). After addition of 1 ml of $KP_i$ and renewed ultrasonic treatment (4×30 sec on ice in 30-sec intervals), 1 ml of 20% BSA (in $KP_i$) was added (final concentration of trioleoylglycerol 1.7 mM). For the reaction, 100 μl of substrate solution were pipetted into 100 μl of HSL solution (HSL prepared as above, diluted in 20 mM $KP_i$, pH 7.0, 1 mM EDTA, 1 mM DTT, 0.02% BSA, 20 μg/ml pepstatin, 10 μg/ml leupeptin) and incubated at 37° C. for 30 min. Addition of 3.25 ml of methanol/chloroform/heptane (10:9:7) and of 1.05 ml of 0.1 M $K_2CO_3$, 0.1 M boric acid (pH 10.5) was followed by thorough mixing and finally centrifugation (800×g, 20 min). After phase separation, one equivalent of the upper phase (1 ml) was removed and the radioactivity was determined by liquid scintillation measurement.

Evaluation:

Substances were normally tested in four independent mixtures. The inhibition of the HSL enzymatic activity by a test substance was determined by comparison with an uninhibited control reaction. The $IC_{50}$ was calculated via an inhibition plot with at least 10 concentrations of the test substance. The data was analyzed using the software package GRAPHIT, Elsevier-BIOSOFT.

Selected compounds of the invention showed the following effect, as measured by this assay:

| Compound of Example No. | $IC_{50}$ (μM) |
|---|---|
| 21 | 10 |
| 22 | 1 |
| 27 | 10 |
| 28 | 6 |
| 30 | 1 |
| 31 | 10 |
| 32 | 3 |
| 33 | 0.2 |
| 34 | 1 |
| 36 | 10 |
| 37 | 1 |
| 38 | 1 |
| 39 | 1 |
| 40 | 10 |
| 41 | 0.1 |
| 42 | 1 |
| 53 | 1 |
| 54 | 1 |
| 58 | 0.8 |
| 60 | 0.2 |
| 62 | 0.3 |
| 65 | 1 |
| 69 | 0.03 |
| 71 | 0.02 |
| 74 | 0.04 |
| 92 | 0.25 |
| 97 | 0.03 |
| 107 | 0.12 |
| 116 | 0.1 |
| 128 | 0.6 |
| 130 | 0.5 |
| 136 | 0.5 |
| 139 | 0.4 |
| 142 | 0.2 |
| 152 | 0.2 |
| 166 | 0.2 |
| 171 | 0.6 |

The following examples illustrate the preparation methods in detail without restricting them.

EXAMPLE 1
3-Methyl-4-nitrophenylhydrazine 5 g of hydrazine hydrate were slowly added dropwise to a solution of 15.9 g of 2-methyl-4-fluoronitrobenzene in 10 ml of N-methylpyrrolidone at room temperature, and the mixture was heated with stirring at 65° C. for 4 hours. The product was precipitated by adding 70 ml of water and was filtered off with suction and then recrystallized from isopropanol.

Yield:13.3 g m.p.: 138° C.

The following examples were prepared in an analogous way:

EXAMPLE 2
3-Fluoro-4-nitrophenylhydrazine
M.p.: 130° C.

EXAMPLE 3
2–Chloro-4-nitrophenylhydrazine
M.p.:144° C.

EXAMPLE 4
2-Methyl-4-nitrophenylhydrazine
M.p.:135° C.

EXAMPLE 5
3-(4-Fluorobenzyloxy)-2-nitrophenylhydrazine
M.p.:164° C.

The starting compound 2-fluoro-4-(4-fluorobenzyloxy) nitrobenzene (m.p.: 99° C.) was prepared by alkylation of 3-fluoro-4-nitrophenol with 4-fluorobenzyl chloride in DMF in the presence of potassium carbonate.

EXAMPLE 6
3-(4-Fluorobenzyloxy)-4-nitrophenylhydrazine (intermediate)
M.p.: 145° C.

EXAMPLE 7
4-(4–Chlorophenoxy)-3-nitroaniline 1.4 g of potassium carbonate were added to a solution of 1.29 g of 4-chlorophenol in 8 ml of DMF and, after stirring for 30 minutes, 1.6 g of 4-fluoro-3-nitroaniline were added, and the mixture was stirred at 100° C. for 3 hours. After cooling, 80 ml of water were added and, after brief stirring, the precipitate was filtered off with suction and dried in vacuo at 40° C.

Yield: 2.0 g; m.p.: 101° C.

EXAMPLE 8
4-(4–Chlorophenoxy)-3-nitrophenylhydrazine

A solution of 0.52 g of sodium nitrite in 5 ml of water was added dropwise to a stirred mixture consisting of 1.9 g of 4-(4-chlorophenoxy)-3-nitroaniline, 25 ml of concentrated hydrochloric acid and 25 ml of ethanol cooled to 0° C., and the mixture was then stirred at 0° C. for 60 min and subsequently added dropwise to a suspension of 8.5 g of tin dichloride dihydrate in 8 ml of concentrated HCl. The precipitate was filtered off with suction, washed with water, suspended in 200 ml of water under nitrogen and decomposed with 100 ml of 30% strength sodium hydroxide solution at 10–15° C. The oil formed was extracted by shaking with ethyl acetate and washed with water, and the organic phase was dried with sodium sulfate. The product was then precipitated with isopropanolic HCl, filtered off with suction and dried in vacuo.

Yield: 1.1 g; m.p.: 221° C.

EXAMPLE 9

Methyl N'-(4-nitro-2-methylphenyl)hydrazinoformate 0.43 ml of methyl chloroformate was cautiously added dropwise to a mixture consisting of 0.84 g of 2-methyl-4-nitrophenylhydrazine, 15 ml of NMP and 2 ml of pyridine while cooling in ice, and the mixture was then stirred for 2 hours while slowly warming to RT. After dilution with 50 ml of water, the mixture was stirred over night and the solid was dried in vacuo at 40° C.

Yield: 0.81 g; m.p.:153° C.

The following examples were prepared in an analogous way:

EXAMPLE 10

Methyl N'-(4-nitrophenyl)hydrazinoformate (intermediate)
M.p.: 179° C.

EXAMPLE 11

Methyl N'-(3-fluoro-4-nitrophenyl)hydrazinoformate
M.p.: 127.4° C.

EXAMPLE 12

Methyl N'-(3-methyl-4-nitrophenyl)hydrazinoformate
M.p.: 159° C.

EXAMPLE 13

Methyl N'-(2-chloro-4-nitrophenyl)hydrazinoformate
M.p.: 156° C.

EXAMPLE 14

Methyl N'-(3-(4-fluorobenzyloxy)-4-nitrophenyl)hydrazinoformate (intermediate)
M.p.: 166° C.

EXAMPLE 15

Methyl N'-(3-(4-fluorobenzyloxy)-2-nitrophenyl)hydrazinoformate
M.p.: 193° C.

EXAMPLE 16

Methyl N'-(4-(4-chlorophenoxy)-3-nitrophenyl)hydrazinoformate
M.p.: 147° C.

EXAMPLE 17

Methyl N'-(3-piperidino-4-nitrophenyl)hydrazinoformate (-)
M.p.: 131° C.

The latter compound and the compound of Example 18 were prepared by reacting methyl N'-(3-fluoro-4-nitrophenyl)hydrazinoformate with piperidine and N-benzyl-piperazine, respectively, in NMP at 80° C.

EXAMPLE 18

Methyl N'-(3-(N-benzylpiperazino)-4-nitrophenyl)hydrazinoformate
M.p.: 156° C.

EXAMPLE 19

5-Methoxy-3-(4-nitrophenyl)-3H-(1,3,4)oxadiazol-2-one 2.5 g of methyl N'-(4-nitrophenyl)hydrazinoformate and 5 ml of pyridine were taken up in 15 ml of methylene chloride and, while stirring and cooling in ice, 3 ml of a 20% strength solution of phosgene in toluene were added dropwise. This mixture was left to stand at room temperature overnight and was diluted with a further 10 ml of methylene chloride and then washed 3 times with water. After drying over sodium sulfate, the mixture was concentrated in vacuo, and the product was purified by column chromatography (silica gel, solvents: methanol:methylene chloride=2:98) and recrystallized from isopropanol.

Yield:1.5 g m.p.: 151° C.

The following examples were prepared analogously to Example 4:

EXAMPLE 20

5-Methoxy-3-(3-methyl-4-nitrophenyl)-3H-(1,3,4)oxadiazol-2-one
M.p.: 112° C.

EXAMPLE 21

5-Methoxy-3-(4-(4-chlorophenoxy-3-nitrophenyl)-3H-(1,3,4)oxadiazol-2-one
M.p.: oil

EXAMPLE 22

5-Methoxy-3-(3-(4-fluorobenzyloxy)-2-nitrophenyl)-3H-(1,3,4)oxadiazol-2-one
M.p.: 99° C.

EXAMPLE 23

5-Methoxy-3-(2-methyl-4-nitrophenyl)-3H-(1,3,4)oxadiazol-2-one
M.p.: 111° C.

EXAMPLE 24

5-Methoxy-3-(3-(4-fluorobenzyloxy)-4-nitrophenyl)-3H-(1,3,4)oxadiazol-2-one
M.p.: 137° C.

EXAMPLE 25

5-Methoxy-3-(4-aminophenyl)-3H-(1,3,4)oxadiazol-2-one

A mixture consisting of 1.4 g of 5-methoxy-3-(4-nitrophenyl)-3H-(1,3,4)oxadiazol-2-one, 0.5 g of Pd/C and 20ml of methanol was hydrogenated under atmospheric pressure at room temperature until the calculated amount of hydrogen had been taken up. The catalyst was then filtered off, and the solution was concentrated in vacuo. The remaining semisolid residue was stirred with isopropanol and filtered off with suction.

Yield: 0.75g; m.p.: 85° C.

EXAMPLE 26

5-Methoxy-3-(2-amino-4-(4-fluorobenzyloxy)phenyl)-3H-(1,3,4)oxadiazol-2-one
M.p.: oil

EXAMPLE 27

5-Methoxy-3-(3-amino-4-(4-chlorophenoxy)phenyl)-3H-(1,3,4)oxadiazol-2-one
M.p.: 133° C.

EXAMPLE 28

5-Methoxy-3-(4-amino-3-methylphenyl)-3H-(1,3,4)oxadiazol-2-one
M.p.: 114° C.

EXAMPLE 29
5-Methoxy-3-(4-amino-3-(4-fluorobenzyloxy)phenyl)-3H-(1,3,4)oxadiazol-2-one
  M.p.: 195° C.

EXAMPLE 30
5-Methoxy-3-(4-(4-chlorophenylacetylamino)phenyl)-3H-(1,3,4)oxadiazol-2-one 201 mg of 4-chlorophenylacetyl chloride were added dropwise to a mixture consisting of 200 mg of 5-methoxy-3-(4-aminophenyl)-3H-(1,3,4)oxadiazol-2-one, 20 ml of methylene chloride and 0.1 ml of pyridine cooled in ice, and the mixture was stirred at room temperature for 5 hours. Volatiles were removed in vacuo. The residue was stirred with water and the solid was filtered off with suction and dried at 40° C. in vacuo.

Yield: 318 mg; m.p.:161° C.

The following examples were prepared in an analogous way:

EXAMPLE 31:
5-Methoxy-3-(4-(4-chlorophenylacetylamino)-3-methylphenyl)-3H-(1,3,4)oxadiazol-2-one
  M.p.: 190° C.

EXAMPLE 32
5-Methoxy-3-(4-octanoylamino-3-methylphenyl)-3H-(1,3,4)oxadiazol-2-one
  M.p.: 110° C.

EXAMPLE 33
5-Methoxy-3-(4-(4-heptylbenzoylamino)phenyl)-3H-(1,3,4)oxadiazol-2-one
  M.p.: 155° C.

EXAMPLE 34
5-Methoxy-3-(4-(4-butylphenylsulfonylamino)phenyl)-3H-(1,3,4)oxadiazol-2-one
  M.p.: 135° C.

EXAMPLE 35
5-Methoxy-3-(4-(4-chlorobutanoylamino)-3-methylphenyl)-3H-(1,3,4)oxadiazol-2-one
  M.p.: 137° C.

EXAMPLE 36
5-Methoxy-3-(4-pivaloylamino-3-methylphenyl)-3H-(1,3,4)oxadiazol-2-one
  M.p.: 157° C.

EXAMPLE 3
5-Methoxy-3-(4-(4-chlorophenylsulfonylamino)-3-methylphenyl)-3H-(1,3,4)oxadiazol-2-one
  M.p.: 147° C.

EXAMPLE 38
5-Methoxy-3-(4-(1-naphthylsulfonylamino)-3-methylphenyl)-3H-(1,3,4)oxadiazol-2-one
  M.p.: 123° C.

EXAMPLE 39
5-Methoxy-3-(4-(2-phenylethenylsulfonylamino)-3-methylphenyl)-3H-(1,3,4)oxadiazol-2-one
  M.p.: 129° C.

EXAMPLE 40
5-Methoxy-3-(4-(2,2,2-trifluoroethylsulfonylamino)-3-methylphenyl)-3H-(1,3,4)oxadiazol-2-one
  M.p.: 151° C.

EXAMPLE 41
5-Methoxy-3-(4-(benzyloxycarbonylamino)-3-methylphenyl)-3H-(1,3,4)oxadiazol-2-one
  M.p.: 115° C.

EXAMPLE 42
5-Methoxy-3-(4-(3,4-dichlorophenylaminocarbonylamino)-3-methylphenyl)-3H-(1,3,4)oxadiazol-2-one
  M.p.: 210° C.

The latter compound was obtained by reacting 5-methoxy-3-(4-amino-3-methylphenyl)-3H-(1,3,4)oxadiazol-2-one with equimolar amounts of 3,4-dichlorophenyl isocyanate in toluene at 50° C.

EXAMPLE 43
5-Methoxy-3-(4-(4-chlorophenylsulfonylamino)phenyl)-3H-(1,3,4)oxadiazol-2-one
  M.p.: 169° C.

EXAMPLE 44
5-Methoxy-3-(4-(2-chlorophenylsulfonylamino)phenyl)-3H-(1,3,4)oxadiazol-2-one
  M.p.: 171° C.

EXAMPLE 45
5-Methoxy-3-(4-(3-chlorophenylsulfonylamino)phenyl)-3H-(1,3,4)oxadiazol-2-one
  M.p.: 141° C.

EXAMPLE 46
5-Methoxy-3-(4-(4-chlorophenylacetylamino)-3-(4-fluorobenzyloxy)phenyl)-3H-(1,3,4)oxadiazol-2-one
  M.p.: 167° C.

EXAMPLE 47
5-Methoxy-3-(4-benzylsulfonylaminophenyl)-3H-(1,3,4)oxadiazol-2-one
  M.p.: 153° C.

EXAMPLE 48
5-Methoxy-3-(4-(-2-(4'-chlorobiphenyl)ethyl)sulfonylamino)phenyl)-3H-(1,3,4)oxadiazol-2-one
  M.p.: 165° C.

EXAMPLE 49
5-Methoxy-3-(4-isopropylsulfonylaminophenyl)-3H-(1,3,4)oxadiazol-2-one
  M.p.: 190° C.

EXAMPLE 50
5-Methoxy-3-(4-dimethylamino-3-methylphenyl)-3H-(1,3,4)oxadiazol-2-one
  M.p.: 71° C.

The latter compound was obtained by reacting 5-methoxy-3-(4-amino-3-methylphenyl)-3H-(1,3,4)oxadiazol-2-one with paraformaldehyde/formic acid in DMF at room temperature and was purified by column chromatography (silica gel, ethyl acetate:n-heptane=1:1).

EXAMPLE 51
5-Methoxy-3-(4-(4-chlorobenzylamino)-3-methylphenyl)-3H-(1,3,4)oxadiazol-2-one
  M.p.: oil The latter compound was obtained by reacting 5-methoxy-3-(4-amino-3-methylphenyl)-3H-(1,3,4)oxadiazol-2-one with 4-chlorobenzaldehyde/sodium borohydride in methanol/methylene chloride at room tempera-

EXAMPLE 52

5-Methoxy-3-(4-(2-oxopyrrolidin-1-yl)-3-methylphenyl)-3H-(1,3,4)oxadiazol-2-one

M.p.: oil

The latter compound was prepared by reacting 5-methoxy-3-(4-(4-chlorobutanoylamino)-3-methylphenyl)-3H-(1,3,4)oxadiazol-2-one with sodium hydride in dioxane at room temperature and purifying the crude product by column chromatography (silica gel, methylene chloride:methanol=98:2).

EXAMPLE 53

5-Methoxy-3-(4-(4-oxopent-2-en-2-ylamino)-3-methylphenyl)-3H-(1,3,4)oxadiazol-2-one M.p.: 143° C.

The latter compound was obtained by reacting 5-methoxy-3-(4-amino-3-methylphenyl)-3H-(1,3,4)oxadiazol-2-one with equimolar amounts of acetylacetone in glacial acetic acid at 80° C. and was isolated by precipitation by adding water and filtration.

EXAMPLE 54

5-Methoxy-3-(4-(2,5-dimethylpyrrol-1-yl)-3-methylphenyl)-3H-(1,3,4)oxadiazol-2-one M.p.: oil The latter compound was obtained by reacting 5-methoxy-3-(4-amino-3-methylphenyl)-3H-(1,3,4)oxadiazol-2-one with equimolar amounts of acetonylacetone in glacial acetic acid at 80° C. Working up took place by dilution with water, extraction by shaking with ethyl acetate and column chromatography (silica gel, methylene chloride) of the crude product obtained after concentration of the dried organic phase.

EXAMPLE 55

5-Methoxy-3-(3-(4-fluorobenzyloxy)-4-methylaminophenyl)-3H-(1,3,4)oxadiazol-2-one M.p.: 98° C.

The latter compound was obtained as a by-product of the hydrogenation of 5-methoxy-3-(3 -(4-fluorobenzyloxy)-4-nitrophenyl)-3H-(1,3,4)oxadiazol-2-one with platinum dioxide as catalyst, in methanol, at room temperature under atmospheric pressure. Purification proceeded by column chromatography (silica gel, methylene chloride) after filtering off the catalyst and concentrating the reaction mixture.

The compounds of Examples 56-199 were prepared analogously to the above-mentioned examples.

EXAMPLE 56

5-Methoxy-3-(3-aminophenyl)-3H-(1,3,4)oxadiazol-2-one

M.p.: 95° C.

EXAMPLE 57

5-Methoxy-3-(3-dibenzylaminophenyl)-3H-(1,3,4)oxadiazol-2-one

M.p.: 71° C.

EXAMPLE 58

5-Methoxy-3-(3-benzylaminophenyl)-3H-(1,3,4)oxadiazol-2-one

M.p.: oil

EXAMPLE 59

5-Methoxy-3-(4-(pyrid-2-yl)aminocarbonylaminophenyl)-3H-(1,3,4)oxadiazol-2-one

M.p.: 81° C.

EXAMPLE 60

5-Methoxy-3-(3-(4-fluorobenzyloxy)-4-benzyloxycarbonylaminophenyl)-3H-(1,3,4)oxadiazol-2-one M.p.: oil

EXAMPLE 61

5-Methoxy-3-(4-amino-2-methylphenyl)-3H-(1,3,4)oxadiazol-2-one

M.p.: oil

EXAMPLE 62

5-Methoxy-3-(3-methyl-4-(2-chlorobenzyloxycarbonylamino)phenyl)-3H-(1,3,4)oxadiazol-2-one M.p.: 161° C.

EXAMPLE 63

5-Methoxy-3-(4-amino-2-chlorophenyl)-3H-(1,3,4)oxadiazol-2-one

M.p.: 126° C.

EXAMPLE 64

5-Methoxy-3-(2-chloro-4-nitrophenyl)-3H-(1,3,4)oxadiazol-2-one

M.p.: 92° C.

EXAMPLE 65

5-Methoxy-3-(2-methyl-4-benzyloxycarbonylaminophenyl)-3H-(1,3,4)oxadiazol-2-one

M.p.: 112° C.

EXAMPLE 66

5-Methoxy-3-(2-methyl-4-(4-trifluoromethoxybenzoylamino)phenyl)-3H-(1,3,4)oxadiazol-2-one M.p.: 150° C.

EXAMPLE 67

5-Methoxy-3-(2-chloro-4-benzyloxycarbonylaminophenyl)-3H-(1,3,4)oxadiazol-2-one

M.p.: 150° C.

EXAMPLE 68

5-Methoxy-3-(3-fluoro-4-nitrophenyl)-3H-(1,3,4)oxadiazol-2-one

M.p.: 127° C.

EXAMPLE 69

5-Methoxy-3-(4-(4-t-butylbenzoylamino)phenyl)-3H-(1,3,4)oxadiazol-2-one

M.p.: 173° C.

EXAMPLE 70

5-Methoxy-3-(4-(4-chlorobenzyloxycarbonylamino)phenyl)-3H-(1,3,4)oxadiazol-2-one M.p.: 177° C.

EXAMPLE 71

5-Methoxy-3-(2-chloro-4-(4-heptylbenzoylamino)phenyl)-3H-(1,3,4)oxadiazol-2-one

M.p.: 135° C.

EXAMPLE 72
5-Methoxy-3-(4-(3,4-dichlorobenzoylamino)phenyl)-3H-(1,3,4)oxadiazol-2-one
M.p.: 200° C.

EXAMPLE 73
5-Methoxy-3-(4-(2-(4-chlorophenoxy)-2-methylpropionylamino)phenyl)-3H-(1,3,4)oxadiazol-2-one
M.p.: 153° C.

EXAMPLE 74
5-Ethoxy-3-(3-methyl-4-benzyloxycarbonylaminophenyl)-3H-(1,3,4)oxadiazol-2-one
M.p.: 94° C.

EXAMPLE 75
5-isopropoxy-3-(3-methyl-4-benzyloxycarbonylaminophenyl)-3H-(1,3,4)oxadiazol-2-one
M.p.: 119° C.

EXAMPLE 76
5-isopropoxy-3-(3-methyl-4-butyloxycarbonylaminophenyl)-3H-(1,3,4)oxadiazol-2-one
M. p.: 114° C.

EXAMPLE 77
5-isopropoxy-3-(3-methyl-4-(3-chlorophenylaminocarbonylamino)phenyl)-3H-(1,3,4)oxadiazol-2-one
M.p.: 201° C.

EXAMPLE 78
5-tert-Butoxy-3-(3-methyl-4-benzyloxycarbonylaminophenyl)-3H-(1,3,4)oxadiazol-2-one
M.p.: 113° C.

EXAMPLE 79
5-Methoxy-3-(3-methyl-4-phenoxycarbonylaminophenyl)-3H-(1,3,4)oxadiazol-2-one
M.p.: 145° C.

EXAMPLE 80
5-Methoxy-3-(3-methyl-4-(pyrid-3-ylcarbonylamino)phenyl)-3H-(1,3,4)oxadiazol-2-one
M.p.: oil

EXAMPLE 81
5-Methoxy-3-(3-methyl-4-(indan-2-ylaminocarbonylamino)phenyl)-3H-(1,3,4)oxadiazol-2-one
M.p.: 206° C.

EXAMPLE 82
5-Methoxy-3-(3-methyl-4-(pyrid-3-ylmethylaminocarbonylamino)phenyl)-3H-(1,3,4)oxadiazol-2-one
M.p.: 229° C.

EXAMPLE 83
5-Methoxy-3-(3-methyl-4-(pyrid-3-ylmethoxycarbonylamino)phenyl)-3H-(1,3,4)oxadiazol-2-one
M.p.: 232° C.

EXAMPLE 84
5-Methoxy-3-(3-fluoro-4-benzyloxycarbonylaminophenyl)-3H-(1,3,4)oxadiazol-2-one
M.p.: oil

EXAMPLE 85
5-Methoxy-3-(3-fluoro-4-(4-trifluoromethylbenzoylamino)phenyl)-3H-(1,3,4)oxadiazol-2-one
M.p.: oil

EXAMPLE 86
5-Methoxy-3-(3-benzyloxy-4-(4-trifluoromethylbenzoylamino)phenyl)-3H-(1,3,4)oxadiazol-2-one
M.p.: 159° C.

EXAMPLE 87
5-Methoxy-3-(3-fluoro-4-(4-tert-butylbenzoylamino)phenyl)-3H-(1,3,4)oxadiazol-2-one
M.p.: 144° C.

EXAMPLE 88
5-Methoxy-3-(3-methyl-4-(2,2,2-trifluoroethoxycarbonylamino)phenyl)-3H-(1,3,4)oxadiazol-2-one
M.p.: 141° C.

EXAMPLE 89
5-Methoxy-3-(3-methyl-4-piperidinocarbonylaminophenyl)-3H-(1,3,4)oxadiazol-2-one
M.p.: 154° C.

EXAMPLE 90
5-Methoxy-3-(4-(6-methoxybenzofuran-2-ylcarbonylamino)phenyl)-3H-(1,3,4)oxadiazol-2-one
M.p.: 191° C.

Further examples of the invention were prepared by the processes described above and characterized by mass spectroscopy (M+1):

| Example No. | Chemical name: | M + 1 | Mol. wt. |
|---|---|---|---|
| 91 | N-[4-(5-Methoxy-2-oxo-[1,3,4]oxadiazol-3-yl)phenyl]-3-methyl-benzenesulfonamide | 362 | 361.4 |
| 92 | 3,4-Dimethoxy-N-[4-(5-methoxy-2-oxo-[1,3,4]oxadiazol-3-yl)-phenyl]benzenesulfonamide | 408 | 407.4 |
| 93 | Quinoline-8-sulfonic acid [4-(5-methoxy-2-oxo-[1,3,4]oxadiazol-3-yl)phenyl]amide | 399 | 398.4 |
| 94 | N-[4-(5-Methoxy-2-oxo-[1,3,4]oxadiazol-3-yl)phenyl]-5-nitro-isophthalic acid monomethyl ester | 415 | 414.3 |
| 95 | 3-(2-Chlorophenyl)-5-methylisoxazole-4-carboxylic acid [4-(5-methoxy-2-oxo-[1,3,4]oxadiazol-3-yl)phenyl]amide | 427 | 426.8 |
| 96 | 3,3,3-Trifluoro-2-methoxy-N-[4-(5-methoxy-2-oxo-[1,3,4]oxadiazol-3-yl)phenyl]-2-phenylpropionamide | 424 | 423.3 |
| 97 | 2-Fluoro-N-[4-(5-methoxy-2-oxo-[1,3,4]oxadiazol-3-yl)phenyl]-benzamide | 330 | 329.3 |
| 98 | Tetradecanoic acid [4-(5-methoxy-2-oxo-[1,3,4]oxadiazol-3-yl)phenyl]amide | 418 | 417.5 |
| 99 | N-[4-(5-Methoxy-2-oxo-[1,3,4]oxadiazol-3-yl)phenyl]-2-phenethyl-benzamide | 416 | 415.4 |
| 100 | N-[4-(5-Methoxy-2-oxo-[1,3,4]oxadiazol-3-yl)phenyl]-2-(4-methoxyphenoxy)-5-nitro-benzamide | 479 | 478.4 |

-continued

| | | | |
|---|---|---|---|
| 101 | 2-(4-Benzyloxyphenyl)-N-[4-(5-methoxy-2-oxo-[1,3,4]oxadiazol-3-yl)phenyl]acetamide | 432 | 431.4 |
| 102 | N-[4-(5-Methoxy-2-oxo-[1,3,4]oxadiazol-3-yl)phenyl]-3,3,3-triphenylpropionamide | 492 | 491.5 |
| 103 | N-[4-(5-Methoxy-2-oxo-[1,3,4]oxadiazol-3-yl)phenyl]-3,5-bis-trifluoromethylbenzamide | 448 | 447.3 |
| 104 | 4-Cyano-N-[4-(5-methoxy-2-oxo-[1,3,4]oxadiazol-3-yl)phenyl]-benzamide | 337 | 336.3 |
| 105 | Nonanoic acid [4-(5-methoxy-2-oxo-[1,3,4]oxadiazol-3-yl)phenyl]amide | 348 | 347.4 |
| 106 | Methyl 9-[4-(5-methoxy-2-oxo-[1,3,4]oxadiazol-3-yl)phenyl-carbamoyl]nonanoate | 406 | 405.4 |
| 107 | Undecanoic acid [4-(5-methoxy-2-oxo-[1,3,4]oxadiazol-3-yl)phenyl]amide | 376 | 375.5 |
| 108 | 4-[4-(5-Methoxy-2-oxo-[1,3,4]oxadiazol-3-yl)phenylcarbamoyl]-benzenesulfonyl fluoride | 394 | 393.3 |
| 109 | 11-Phenoxyundecanoic acid [4-(5-methoxy-2-oxo-[1,3,4]-oxadiazol-3-yl)phenyl]amide | 468 | 467.6 |
| 110 | N-[4-(5-Methoxy-2-oxo-[1,3,4]oxadiazol-3-yl)phenyl]-2,3-diphenylpropionamide | 416 | 415.4 |
| 111 | 4-Chloro-N-[4-(5-methoxy-2-oxo-[1,3,4]oxadiazol-3-yl)phenyl]-2-methylbenzamide | 360 | 359.8 |
| 112 | 6-Chloro-N-[4-(5-methoxy-2-oxo-[1,3,4]oxadiazol-3-yl)phenyl]nicotinamide | 347 | 346.7 |
| 113 | 5-Fluoro-N-[4-(5-methoxy-2-oxo-[1,3,4]oxadiazol-3-yl)phenyl]-2-methylbenzamide | 344 | 343.3 |
| 114 | N-[4-(5-Methoxy-2-oxo-[1,3,4]oxadiazol-3-yl)phenyl]-2,4,6-trimethylbenzamide | 354 | 353.4 |
| 115 | N-[4-(5-Methoxy-2-oxo-[1,3,4]oxadiazol-3-yl)phenyl]-3-naphthalen-2-ylacrylamide | 388 | 387.4 |
| 116 | 5-Oxo-5-phenylpentanoic acid [4-(5-methoxy-2-oxo-[1,3,4]-oxadiazol-3-yl)phenyl]amide | 382 | 381.4 |
| 117 | 3-(2,4-Dichlorobenzylsulfanyl)thiophene-2-carboxylic acid [4-(5-methoxy-2-oxo-[1,3,4]oxadiazol-3-yl)phenyl]amide | 509 | 508.4 |
| 118 | 2-Fluoro-N-[4-(5-methoxy-2-oxo-[1,3,4]oxadiazol-3-yl)phenyl]-4-trifluoromethyl-benzamide | 398 | 397.3 |
| 119 | 1-Hexyl-3-[3-(5-methoxy-2-oxo-[1,3,4]oxadiazol-3-yl)phenyl]urea | 335 | 334.4 |
| 120 | 1-(4-Bromophenyl)-3-[3-(5-methoxy-2-oxo-[1,3,4]oxadiazol-3-yl)phenyl]urea | 406 | 405.2 |
| 121 | 1-[3-(5-Methoxy-2-oxo-[1,3,4]oxadiazol-3-yl)phenyl]-3-(2-methoxyphenyl)urea | 357 | 356.3 |
| 122 | Ethyl 2-[3-[3-(5-methoxy-2-oxo-[1,3,4]oxadiazol-3-yl)phenyl]-ureido]-3-phenyl-propionate | 427 | 426.4 |
| 123 | 1-(2,6-Diisopropylphenyl)-3-[3-(5-methoxy-2-oxo-[1,3,4]oxadiazol-3-yl)phenyl]urea | 411 | 410.5 |
| 124 | 1-[3-(5-Methoxy-2-oxo-[1,3,4]oxadiazol-3-yl)phenyl]-3-octylurea | 363 | 362.4 |
| 125 | 1-(4-Fluorobenzyl)-3-[3-(5-methoxy-2-oxo-[1,3,4]oxadiazol-3-yl)phenyl]urea | 359 | 358.3 |
| 126 | 1-(2-Ethylphenyl)-3-[3-(5-methoxy-2-oxo-[1,3,4]oxadiazol-3-yl)phenyl]urea | 355 | 354.4 |
| 127 | Ethyl 6-[3-[3-(5-methoxy-2-oxo-[1,3,4]oxadiazol-3-yl)phenyl]-ureido]hexanoate | 393 | 392.4 |
| 128 | 1-(2,6-Dimethoxyphenyl)-3-[3-(5-methoxy-2-oxo-[1,3,4]oxadiazol-3-yl)phenyl]urea | 387 | 386.4 |
| 129 | 5-Methoxy-3-[4-[(thiophen-3-ylmethyl)amino]phenyl]-3H-[1,3,4]oxadiazol-2-one | 304 | 303.3 |
| 130 | 4-[[4-(5-Methoxy-2-oxo-[1,3,4]oxadiazol-3-yl)phenylamino]methyl]-benzonitrile trifluoroacetate | 437 | 436.3 |
| 131 | 3-[4-(2-Bromo-4,5-dimethoxybenzylamino)phenyl]-5-methoxy-3H-[1,3,4]oxadiazol-2-one | 437 | 436.3 |
| 132 | 3-[4-(3-Ethoxy-4-methoxybenzylamino)phenyl]-5-methoxy-3H-[1,3,4]oxadiazol-2-one trifluoroacetate | 486 | 485.4 |
| 133 | Methyl 4-[[4-(5-methoxy-2-oxo-[1,3,4]oxadiazol-3-yl)phenylamino]methyl]benzoate trifluoroacetate | 470 | 469.4 |
| 134 | 4-[[4-(5-Methoxy-2-oxo-[1,3,4]oxadiazol-3-yl)phenylamino]-methyl]phenyl acetate | 356 | 355.3 |
| 135 | 5-Methoxy-3-[4-(pentafluorophenylmethyl-amino)phenyl]-3H-[1,3,4]oxadiazol-2-one | 388 | 387.3 |
| 136 | 3-[4-(4-Benzyloxybenzylamino)phenyl]-5-methoxy-3H-[1,3,4]oxadiazol-2-one trifluoroacetate | 518 | 517.5 |
| 137 | 3-[4-(3,3-Dichlorononylamino)phenyl]-5-methoxy-3H-[1,3,4]oxadiazol-2-one trifluoroacetate | 517 | 516.3 |
| 138 | 2-[[4-(5-Methoxy-2-oxo-[1,3,4]oxadiazol-3-yl)phenylamino]-methyl]benzonitrile | 323 | 322.3 |
| 139 | 3-[4-(Cyclohexylmethylamino)phenyl]-5-methoxy-3H-[1,3,4]oxadiazol-2-one | 304 | 303.4 |
| 140 | 5-Methoxy-3-[4-(2,3,5-trichlorobenzyl-amino)phenyl]-3H-[1,3,4]oxadiazol-2-one trifluoroacetate | 515 | 514.7 |
| 141 | 3-[4-(5-Bromo-2-fluorobenzylamino)phenyl]-5-methoxy-3H-[1,3,4]oxadiazol-2-one trifluoroacetate | 509 | 508.2 |
| 142 | 3-[4-(4-Hexyloxybenzylamino)phenyl]-5-methoxy-3H-[1,3,4]oxadiazol-2-one trifluoroacetate | 512 | 511.5 |
| 143 | 5-Methoxy-3-[4-[3-(3-trifluoromethyl-phenoxy)benzylamino]-phenyl]-3H-[1,3,4]oxadiazol-2-one trifluoroacetate | 572 | 571.4 |
| 144 | 3-[4-[(2-Chloroquinolin-3-ylmethyl)amino]phenyl]-5-methoxy-3H-[1,3,4]oxadiazol-2-one trifluoroacetate | 497 | 496.8 |
| 145 | Methyl 3-methoxy-5-[[4-(5-methoxy-2-oxo-[1,3,4]oxadiazol-3-yl)phenylamino]methyl]pyridine-2-carboxylate trifluoroacetate | 501 | 500.4 |
| 146 | 4-[[4-(5-Methoxy-2-oxo-[1,3,4]oxadiazol-3-yl)phenylamino]-methyl]phenyl benzenesulfonate | 454 | 453.5 |
| 147 | 2-(2,6-Dimethyl-4-methylsulfanylphenoxy)-N-[3-(5-methoxy-2-oxo-[1,3,4]oxadiazol-3-yl)phenyl]acetamide | 416 | 415.5 |
| 148 | 1-(2,4-Difluorophenyl)-3-[4-(5-methoxy-2-oxo-[1,3,4]oxadiazol-3-yl)phenyl]urea | 363 | 362.3 |
| 149 | 1-[4-(5-Methoxy-2-oxo-[1,3,4]oxadiazol-3-yl)phenyl]-3-(4-phenoxyphenyl)urea | 419 | 418.4 |
| 150 | 1-(2,6-Difluorophenyl)-3-[4-(5-methoxy-2-oxo-[1,3,4]oxadiazol-3-yl)phenyl]urea | 363 | 362.3 |
| 151 | 1-Butyl-3-[4-(5-methoxy-2-oxo-[1,3,4]oxadiazol-3-yl)phenyl]urea | 307 | 306.3 |
| 152 | 1-(2-Ethoxyphenyl)-3-[4-(5-methoxy-2-oxo-[1,3,4]oxadiazol-3-yl)phenyl]urea | 371 | 370.4 |
| 153 | 1-(2,6-Dibromo-4-fluorophenyl)-3-[4-(5-methoxy-2-oxo-[1,3,4]oxadiazol-3-yl)phenyl]urea | 503 | 502.1 |
| 154 | 1-(4-Butoxyphenyl)-3-[4-(5-methoxy-2-oxo-[1,3,4]oxadiazol-3-yl)phenyl]urea | 399 | 398.4 |
| 155 | 1-[4-(5-Methoxy-2-oxo-[1,3,4]oxadiazol-3-yl)phenyl]-3-(4-trifluoromethoxyphenyl)urea | 411 | 410.3 |
| 156 | 1-Benzyl-3-[4-(5-methoxy-2-oxo-[1,3,4]oxadiazol-3-yl)phenyl]urea | 341 | 340.3 |
| 157 | 1-(3-Fluorophenyl)-3-[4-(5-methoxy-2-oxo-[1,3,4]oxadiazol-3-yl)phenyl]urea | 345 | 344.3 |
| 158 | Ethyl 6-[3-[4-(5-methoxy-2-oxo-[1,3,4]oxadiazol-3-yl)phenyl-ureido]hexanoate | 393 | 392.4 |
| 159 | 1-Biphenyl-4-yl-3-[4-(5-methoxy-2-oxo-[1,3,4]oxadiazol-3-yl)phenyl]urea | 403 | 402.4 |
| 160 | Butyl 2-[3-[4-(5-methoxy-2-oxo-[1,3,4]oxadiazol-3-yl)phenyl-ureido]benzoate | 427 | 426.4 |
| 161 | 5-Methoxy-3-[3-(7-methoxy-3,7-dimethyl-octylamino)phenyl]-3H-[1,3,4]oxadiazol-2-one trifluoroacetate | 492 | 491.5 |
| 162 | 5-Methoxy-3-[3-[(thiophen-2-ylmethyl)amino]phenyl]-3H-[1,3,4]oxadiazol-2-one trifluoroacetate | 418 | 417.4 |
| 163 | 3-(3-Hexylaminophenyl)-5-methoxy-3H-[1,3,4]oxadiazol-2-one trifluoroacetate | 406 | 405.4 |
| 164 | 5-Methoxy-3-[3-(3-phenylpropylamino)phenyl]-3H-[1,3,4]oxadiazol-2-one trifluoroacetate | 440 | 439.4 |
| 165 | 5-Methoxy-3-(3-undecylaminophenyl)-3H-[1,3,4]oxadiazol-2-one trifluoroacetate | 476 | 475.5 |
| 166 | 5-Methoxy-3-[3-[(3-trifluoromethylphenoxy)benzylamino]phenyl]-3H-[1,3,4]oxadiazol-2-one trifluoroacetate | 572 | 571.4 |

-continued

| | | | M.p. ° C. |
|---|---|---|---|
| 167 | 3-[3-[(2-Chloroquinolin-3-ylmethyl)amino]phenyl]-5-methoxy-3H-[1,3,4]oxadiazol-2-one trifluoroacetate | 497 | 496.8 |
| 168 | 4-[[3-(5-Methoxy-2-oxo-[1,3,4]oxadiazol-3-yl)phenylamino]-methyl]phenyl 4-fluorobenzenesulfonate trifluoroacetate | 586 | 585.5 |
| 169 | 5-Methoxy-3-[3-(3,4,5-trifluorobenzylamino)phenyl]-3H-[1,3,4]oxadiazol-2-one trifluoroacetate | 466 | 465.3 |
| 170 | 3-[3-(3,5-Bistrifluoromethylbenzylamino)phenyl]-5-methoxy-3H-[1,3,4]oxadiazol-2-one trifluoroacetate | 548 | 547.3 |
| 171 | 3-(3-Dec-4-enylaminophenyl)-5-methoxy-3H-[1,3,4]oxadiazol-2-one trifluoroacetate | 460 | 459.5 |
| 172 | 3-[3-(3-Cyclopentyl-2-phenethyloxybenzylamino)phenyl]-5-methoxy-3H-[1,3,4]oxadiazol-2-one trifluoroacetate | 600 | 599.6 |
| 173 | 4-[[3-(5-Methoxy-2-oxo-[1,3,4]oxadiazol-3-yl)phenylamino]methyl]-benzonitrile trifluoroacetate | 437 | 436.3 |
| 174 | 5-Methoxy-3-[3-[(6-methylpyridin-2-ylmethyl)amino]phenyl]-3H-[1,3,4]oxadiazol-2-one trifluoroacetate | 427 | 426.3 |
| 175 | 3-[3-(2-Benzyloxyethylamino)phenyl]-5-methoxy-3H-[1,3,4]oxadiazol-2-one trifluoroacetate | 456 | 455.4 |
| 176 | 3-[3-(2,6-Difluorobenzylamino)phenyl]-5-methoxy-3H-[1,3,4]oxadiazol-2-one trifluoroacetate | 448 | 447.3 |
| 177 | Dodecanoic acid [4-(5-methoxy-2-oxo-[1,3,4]oxadiazol-3-yl)phenyl]amide | | 93 |
| 178 | Octadec-9-enoic acid [4-(5-methoxy-2-oxo-[1,3,4]oxadiazol-3-yl)phenyl]-amide | | 67 |
| 179 | 2-Methoxyethyl [4-(5-methoxy-2-oxo-[1,3,4]oxadiazol-3-yl)-2-methylphenyl]carbamate | | 117 |
| 180 | 1-(4-Hydroxycyclohexyl)-3-[4-(5-methoxy-2-oxo-[1,3,4]oxadiazol-3-yl)-2-methylphenyl]urea | | 220 |
| 181 | 1,1-Dibutyl-3-[4-(5-methoxy-2-oxo-[1,3,4]oxadiazol-3-yl)-2-methyl-phenyl]urea | | Oil |
| 182 | 5-Methoxybenzofuran-2-carboxylic acid [4-(5-methoxy-2-oxo-[1,3,4]oxadiazol-3-yl)-2-methylphenyl]amide | | 199 |
| 183 | 4-Methylpiperazine-1-carboxylic acid [4-(5-methoxy-2-oxo-[1,3,4]oxadiazol-3-yl)-2-methylphenyl]amide | | Oil |
| 184 | 1-Methylpiperidin-4-yl [4-(5-methoxy-2-oxo-[1,3,4]oxadiazol-3-yl)-2-methylphenyl]carbamate | | 235 |
| 185 | Cyclohexyl [4-(5-methoxy-2-oxo-[1,3,4]oxadiazol-3-yl)-2-methylphenyl]-carbamate | | 163 |
| 186 | 4-Benzylpiperidine-1-carboxylic acid [4-(5-methoxy-2-oxo-[1,3,4]oxadiazol-3-yl)-2-methyl-phenyl]amide | | 146 |
| 187 | 1-(2-Diisopropylaminoethyl)-3-[4-(5-methoxy-2-oxo-[1,3,4]oxadiazol-3-yl)-2-methylphenyl]urea | | 136 |
| 188 | 4-(2-{3-[4-(5-Methoxy-2-oxo-[1,3,4]oxadiazol-3-yl)-2-methylphenyl]-ureido}ethyl)benzenesulfonamide | | 200 |
| 189 | 1-(1-Benzylpiperidin-4-yl)-3-[4-(5-methoxy-2-oxo-[1,3,4]oxadiazol-3-yl)-2-methylphenyl]urea | | 198 |
| 190 | 1-(4-Isopropylphenyl)-3-[4-(5-methoxy-2-oxo-[1,3,4]oxadiazol-3-yl)-2-methylphenyl]urea | | 200 |
| 191 | 2-{3-[4-(5-Methoxy-2-oxo-[1,3,4]oxadiazol-3-yl)-2-methylphenyl]ureido}-3-methylbutyric acid | | 246 |
| 192 | 1,2,3,4-Tetrahydronaphth-1-yl [4-(5-methoxy-2-oxo-[1,3,4]oxadiazol-3-yl)-2-methylphenyl]carbamate | | 159 |
| 193 | 1-Phenylethyl [4-(5-methoxy-2-oxo-{1,3,4]oxadiazol-3-yl)-2-methyl-phenyl]carbamate | | Oil |
| 194 | 4-Isopropylbenzyl [4-(5-methoxy-2-oxo-[1,3,4]oxadiazol-3-yl)-2-methylphenyl]carbamate | | 88 |
| 195 | 4-Trifluoromethoxybenzyl [4-(5-methoxy-2-oxo-[1,3,4]oxadiazol-3-yl)-2-methylphenyl]carbamate | | 82 |
| 196 | 3,5-Dichlorobenzyl [4-(5-methoxy-2-oxo-[1,3,4]oxadiazol-3-yl)-2-methylphenyl]carbamate | | 169 |
| 197 | Biphenyl-2-ylmethyl [4-(5-methoxy-2-oxo-[1,3,4]oxadiazol-3-yl)-2-methylphenyl]carbamate | | 138 |
| 198 | 5-Chlorobenzofuran-2-carboxylic acid-[4-(5-methoxy-2-oxo-[1,3,4]oxadiazol-3-yl)-2-methyl-phenyl]amide | | 210 |
| 199 | 5-Chlorobenzofuran-2-carboxylic acid [4-(5-methoxy-2-oxo-[1,3,4]oxadiazol-3-yl)phenyl]amide | | 209 |

We claim:

1. Compounds of the formula 1

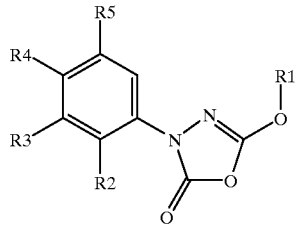

(1)

in which:

$R^1$ is $C_1$–$C_6$-alkyl, $C_3$–$C_9$-cycloalkyl, wherein both groups are optionally substituted one or more times by phenyl, $C_1$–$C_4$-alkyloxy, S—$C_1$–$C_4$-alkyl, N($C_1$–$C_4$-alkyl)$_2$, and wherein phenyl is optionally substituted one or more times by halogen, $C_1$–$C_4$-alkyl, $C_1$–$C_4$-alkyloxy, nitro, $CF_3$; and $R^2$, $R^3$, $R^4$ and $R^5$ independently of one another are hydrogen, halogen, nitro, $C_1$–$C_4$-alkyl, $C_1$–$C_9$-alkyloxy; $C_6$–$C_{10}$-aryl-$C_1$–$C_4$-alkyloxy, $C_6$–$C_{10}$-aryloxy, $C_6$–$C_{10}$-aryl, $C_3$–$C_8$-cycloalkyl or O—$C_3$–$C_8$-cycloalkyl, each of which is optionally substituted once, twice or three times by halogen, $CF_3$, $C_1$–$C_4$-alkyloxy or $C_1$–$C_4$-alkyl; 2-oxopyrrolidin-1-yl, 2,5-dimethylpyrrol-1-yl or $NR^6$-A-$R^7$, with the proviso that $R^2$, $R^3$, $R^4$ and $R^5$ are not simultaneously hydrogen, and at least one of the radicals $R^2$, $R^3$, $R^4$ or $R^5$ is the radical 2-oxopyrrolidin-1-yl, 2,5-dimethylpyrrol-1-yl, or $NR^6$-A-$R^7$, and wherein:

$R^6$ is hydrogen, $C_1$–$C_4$-alkyl or $C_6$–$C_{10}$-aryl-$C_1$–$C_4$-alkyl, where aryl may be substituted by halogen, $CF_3$, $C_1$–$C_8$-alkyloxy or $C_1$–$C_4$-alkyl;

A is a single bond, $CO_n$, $SO_n$, or $CONH$;

n is 1 or 2;

$R^7$ is hydrogen;

$C_1$–$C_{18}$-alkyl or $C_2$–$C_{18}$-alkenyl, wherein $C_1$–$C_{18}$-alkyl or $C_2$–$C_{18}$-alkenyl are optionally substituted one to three times by $C_1$–$C_4$-alkyl, halogen, $CF_3$, $C_1$–$C_4$-alkyloxy, N($C_1$–$C_4$-alkyl)$_2$, —COOH, $C_1$–$C_4$-alkyloxycarbonyl, $C_6$–$C_{12}$-aryl, $C_6$–$C_{12}$-aryloxy, $C_6$–$C_{12}$-arylcarbonyl, $C_6$–$C_{10}$-aryl-$C_1$–$C_4$-alkyloxy or oxo, wherein aryl is in turn optionally substituted by halogen, $C_1$–$C_4$-alkyl, aminosulfonyl or methylmercapto;

$C_6$–$C_{10}$-aryl-$C_1$–$C_4$-alkyl, $C_5$–$C_8$-cycloalkyl-$C_1$–$C_4$-alkyl, $C_5$–$C_8$-cycloalkyl, $C_6$–$C_{10}$-aryl-$C_2$–$C_6$-alkenyl, $C_6$–$C_{10}$-aryl, biphenylyl, biphenylyl-$C_1$–$C_4$-alkyl, indanyl, each of which is optionally substituted once or twice by $C_1$–$C_{18}$-alkyl, $C_1$–$C_{18}$-alkyloxy, $C_3$–$C_8$-cycloalkyl, COOH, hydroxyl, $C_1$–$C_4$-alkylcarbonyl, $C_6$–$C_{10}$-aryl- $C_1$–$C_4$-alkyl, $C_6$–$C_{10}$-aryl-$C_1$–$C_4$-alkyloxy, $C_6$–$C_{10}$-aryloxy, nitro, cyano, $C_6$–$C_{10}$-aryl, fluorosulfonyl, $C_1$–$C_6$-alkyloxycarbonyl, $C_6$–$C_{10}$-arylsulfonyloxy, pyridyl, $NHSO_2$–$C_6$–$C_{10}$-aryl, halogen, $CF_3$ or $OCF_3$, wherein alkyl is in turn optionally substituted by $C_1$–$C_4$-alkyloxycarbonyl, $CF_3$ or carboxyl, and aryl is also optionally substituted by halogen, $CF_3$ or $C_1$–$C_4$-alkyloxy;

or the group Het-$(CH_2)_r$—,
wherein r=0, 1, 2 or 3 and Het=a saturated or unsaturated 5–7-membered heterocycle, optionally benzo-fused and optionally substituted by $C_1$–$C_4$-alkyl, $C_6$–$C_{10}$-aryl, halogen, $C_1$–$C_4$-alkyloxy, $C_1$–$C_4$-alkyloxycarbonyl, $C_6$–$C_{10}$-aryl-$C_1$–$C_4$-alkyl, $C_6$–$C_{10}$-aryl-$C_1$–$C_4$-alkylmercapto or nitro, wherein the benzo-fused aryl is in turn optionally substituted by halogen, $C_1$–$C_4$-alkyloxy or $CF_3$ and the alkyl in arylalkyl is also optionally by methoxy and $CF_3$, and their pharmaceutically acceptable salts and acid addition salts.

2. Compounds of the formula 1 as claimed in claim 1, in which $R^1$ is $C_1$–$C_4$-alkyl.

3. Compounds of the formula 1 as claimed in claim 1, in which $R^1$ is methyl.

4. Compounds of the formula 1 as claimed in claim 1, in which $R^5$ is hydrogen.

5. Compounds of the formula 1 as claimed in claim 1, in which $R^2$ is hydrogen, halogen, $C_1$–$C_4$-alkyl, $C_1$–$C_9$-alkyloxy or amino.

6. Compounds of the formula 1 as claimed in claim 1, in which $R^3$ is hydrogen, $C_1$-$C_4$-alkyl, $C_6$–$C_{10}$-aryl-$C_1$–$C_4$-alkyloxy, which is optionally substituted in the aryl moiety by halogen, or is $NR^6$-A-$R^7$ wherein
$R^6$=hydrogen or benzyl,
A=single bond and
$R^7$=$C_6$–$C_{10}$-aryl-$C_1$–$C_4$-alkyl, which is optionally substituted by halogen, $CF_3$, cyano, phenyl-$C_1$–$C_4$-alkyloxy, $CF_3$-phenoxy, $C_5$–$C_8$-cycloalkyl or fluorosulfonyloxy;
$C_1$–$Ci_2$-alkyl, which is optionally substituted by $C_1$–$C_4$-alkyloxy, phenyl, $CF_3$ or phenyl-$C_1$–$C_4$-alkyloxy;
$C_2$–$C_{12}$-alkenyl or the group Het-$(CH_2)_r$—,
wherein r=0 or 1, and Het=a saturated or unsaturated 5–7-membered heterocycle, which is optionally benzo-fused and optionally substituted by $C_1$–$C_4$-alkyl or halogen.

7. Compounds of the formula 1 as claimed in claim 1, in which $R^4$ is hydrogen, 2-oxopyrrolidin-1-yl, 2,5-dimethylpyrrol-1-yl, or $C_6$–$C_{10}$-aryl-$C_1$–$C_4$-alkyloxy, which is optionally substituted by halogen.

8. Compounds of the formula 1 as claimed in claim 1, in which:
$R^4$ is $NR^6$-A-$R^7$, wherein
$R^6$=hydrogen or methyl,
A=single bond and
$R^7$=hydrogen;
$C_1$–$C_{12}$-alky, which is optionally substituted once or twice by halogen;
$C_2$–$C_{18}$-alkenyl, which is optionally substituted once or twice by $C_1$–$C_4$-alkyl or $C_1$–$C_4$-alkyloxycarbonyl;
$C_6$–$C_{10}$-aryl-$C_1$–$C_4$-alky, which is optionally substituted by halogen, $C_1$–$C_6$-alkyloxy, $CF_3$, cya no, $C_5$–$C_6$-cycloalkyl, $C_1$–$C_4$-alkyloxycarbonyl, $C_6$–$C_{10}$-aryl-$C_1$–$C_4$-alkyl, $C_6$–$C_{10}$-aryl-$C_1$–$C_4$-alkyloxy, wherein aryl is further optionally substituted by halogen or $CF_3$;
$C_5$–$C_8$-cycloalkyl-$C_1$–$C_4$-alkyl ; or
the group Het-$(CH_2)$r—,
wherein r=1, 2 or 3 and Het=a saturated or unsaturated 5–7-membered heterocycle, which is optionally substituted by halogen, $C_1$–$C_4$-alkyloxy or $C_1$–$C_4$-alkyloxycarbonyl.

9. Compounds of the formula 1 as claimed in claim 1, in which:
$R^4$ is $NR^6$-A-$R^7$ wherein
$R^6$=hydrogen,
A=—CO— and
$R^7$ $C_1$–$C_{18}$-alkyl, which is optionally substituted by halogen, phenyl, phenoxy, phenylcarbonyl or $C_1$–$C_4$-alkyloxycarbonyl, wherein phenoxy is optionally substituted by methyl, halogen or methylmercapto;
$C_2$–$C_{18}$-alkenyl, which is optionally substituted by $C_6$–$C_{10}$-aryl;
$C_6$–$C_{10}$-aryl, which is optionally substituted by halogen, $C_1$–$C_8$-alkyl, phenyl-$C_1$–$C_4$-alkyl, $CF_3$, $OCF_3$, fluorosulfonyl, $C_1$–$C_4$-alkyloxycarbonyl, phenoxy, wherein aryl is optionally substituted by $C_1$–$C_4$-alkyloxy;
$C_6$–$C_{10}$-aryl-$C_1$–$C_4$-alkyl, wherein alkyl is optionally substituted by methoxy or $CF_3$ and aryl by halogen; or
the group Het-$(CH_2)_r$—,
wherein r=0 and Het=a saturated or unsaturated 5–7-membered heterocycle, which is optionally benzo-fused and optionally substituted by $C_1$–$C_4$-alkyl, halogen, $C_1$–$C_4$-alkyloxy, halophenyl or halobenzylmercapto, wherein benzo-fused aryl is optionally substituted by halogen or methoxy.

10. Compounds of the formula 1 as claimed in claim 1, in which:
$R^4$ is $NR^6$-A-$R^7$, wherein
$R^6$=hydrogen,
A=—$CO_2$— and
$R^7$=$C_1$–$C_{18}$-alkyl, which is substituted by $CF_3$ or phenyl;
$C_6$–$C_{10}$-aryl;
$C_6$–$C_{10}$-aryl-$C_1$–$C_4$-alkyl, which is substituted by $C_1$–$C_4$-alkyl, halogen, $CF_3$ or $OCF_3$, benzyloxy or phenyl; or
the group Het-$(CH_2)_r$—,
wherein r=0 or 1 and Het=a saturated or unsaturated 5–7-membered heterocycle, which is optionally benzo-fused and optionally substituted by $C_1$–$C_4$-alkyl or benzyl.

11. Compounds of the formula 1 as claimed in claim 1, in which:
$R^4$ is $NR^6$-A-R, wherein
$R^6$=hydrogen,
A=—$SO_2$— and
$R^7$=$C_1$–$C_6$-alky, which is optionally substituted by $CF_3$;
$C_2$–$C_4$-alkenyl, which is optionally substituted by phenyl;
$C_6$–$C_{10}$-aryl, which is optionally substituted by $C_1$–$C_6$-alkyl, halogen, $C_1$–$C_4$-alkyloxy or benzyl;
biphenylyl-$C_1$–$C_4$-alkyl substituted by halogen; or
the group Het-$(CH_2)_r$—,
wherein r=0 and Het=a saturated or unsaturated 5–7-membered heterocycle.

12. Compounds of the formula 1 as claimed in claim 1, in which:

R⁴ is NR⁶-A-R⁷, wherein
R⁶=hydrogen,
A=—CO—NH— and
R⁷=$C_1$-$C_{10}$-alkyl, which is optionally substituted by $C_1$-$C_4$-alkyloxycarbonyl, N($C_1$-$C_4$-alkyl)$_2$ or phenyl, which is in turn optionally substituted by halogen or aminosulfonyl;
$C_6$-$C_{10}$-aryl, which is optionally substituted by $C_1$-$C_6$-alkyl, $C_1$-$C_6$-alkyloxy, $C_1$-$C_6$-alkyloxycarbonyl, phenoxy, $OCF_3$, benzyl or pyridyl, wherein alkyl is optionally substituted by $C_1$-$C_4$-alkyloxycarbonyl or carboxyl;
$C_5$-$C_8$-cycloalky, which is optionally substituted by hydroxyl, or indanyl; or
the group Het-(CH2)r—,
wherein r=0 or 1 and Het=a saturated or unsaturated 5–7-membered heterocycle, which is optionally substituted by benzyl.

13. A process for preparing compounds of the formula 1 as claimed in any one of claims 1 to 12, comprising the steps of:

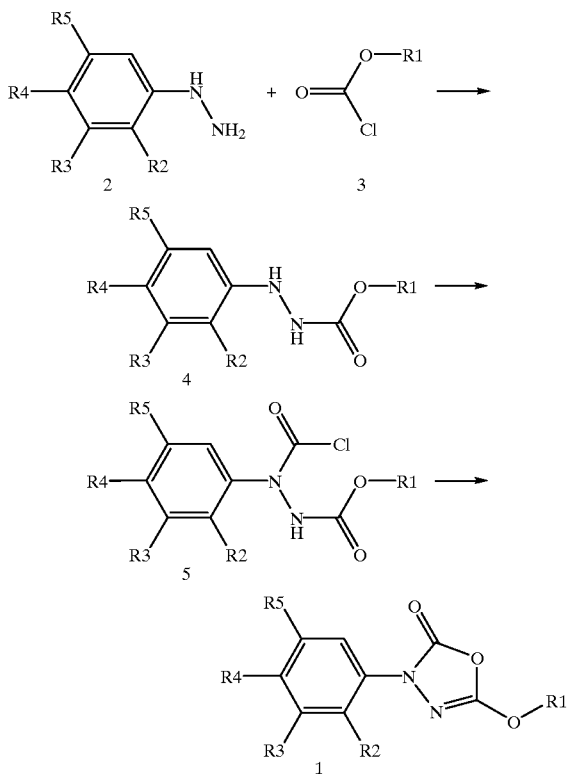

reacting hydrazines of the formula 2 with chloroformic esters of the formula 3 or other reactive carbonic ester derivatives in which $R^1$, $R^2$, $R^3$, $R^4$ and $R^5$ are as defined in claim 1 to give the compounds of the formula 4,
acylating the compounds of the formula 4 with phosgene, carbonyldiimidazole, diphosgene or triphosgene, to give the compounds of the formula 5, and
cyclizing the compounds of the formula 5 into the compounds of the formula 1.

14. A process according to claim 13 further comprising the step of reacting said compounds of formula 1 with a suitable agent to form pharmaceutically acceptable salts or acid addition salts.

15. A process according to claim 13, further comprising the step of chemical modification of the radicals $R_2$–$R_5$ by reduction of nitro to amino radicals, acylation or alkylation.

16. A process according to claim 15 further comprising the step of reacting said compounds of formula 1 with a suitable agent to form pharmaceutically acceptable salts or acid addition salts.

17. A pharmaceutical composition for treating non-insulin-dependent diabetes mellitus or diabetic syndrome, comprising at least one of the compounds of formula 1 as claimed in any one of claims 1 to 12.

18. A method of inhibiting hormone-sensitive lipase, comprising administering to a patient in need thereof at least one compound of the formula 1 as claimed in claim 1.

19. A method of inhibiting hormone-sensitive lipase, comprising administering to a patient in need thereof at least one compound of the formula 1 is claimed in claim 2.

20. A method of inhibiting hormone-sensitive lipase, comprising administering to a patient in need thereof at least one compound of the formula 1 as claimed in claim 3.

21. A method of inhibiting hormone-sensitive lipase, comprising administering to a patient in need thereof at least one compound of the formula 1 as claimed in claim 4.

22. A method of inhibiting hormone-sensitive lipase, comprising administering to a patient in need thereof at least one compound of the formula 1 as claimed in claim 5.

23. A method of inhibiting hormone-sensitive lipase, comprising administering to a patient in need thereof at least one compound of the formula 1 as claimed in claim 6.

24. A method of inhibiting hormone-sensitive lipase, comprising administering to a patient in need thereof at least one compound of the formula 1 as claimed in claim 7.

25. A method of inhibiting hormone-sensitive lipase, comprising administering to a patient in need thereof at least one compound of the formula 1 as claimed in claim 8.

26. A method of inhibiting hormone-sensitive lipase, comprising administering to a patient in need thereof at least one compound of the formula 1 as claimed in claim 9.

27. A method of inhibiting hormone-sensitive lipase, comprising administering to a patient in need thereof at least one compound of the formula 1 as claimed in claim 10.

28. A method of inhibiting hormone-sensitive lipase, comprising administering to a patient in need thereof at least one compound of the formula 1 as claimed in claim 11.

29. A method of inhibiting hormone-sensitive lipase, comprising administering to a patient in need thereof at least one compound of the formula 1 as claimed in claim 12.

30. A method of treating non-insulin dependent diabetes mellitus or diabetic syndrome, comprising administering to a patient in need thereof at least one compound of the formula 1 as claimed in claim 1.

31. A method of treating non-insulin dependent diabetes mellitus or diabetic syndrome, comprising administering to a patient in need thereof at least one compound of the formula 1 as claimed in claim 2.

32. A method of treating non-insulin dependent diabetes mellitus or diabetic syndrome, comprising administering to a patient in need thereof at least one compound of the formula 1 as claimed in claim 3.

33. A method of treating non-insulin dependent diabetes mellitus or diabetic syndrome, comprising administering to a patient in need thereof at least one compound of the formula 1 as claimed in claim 4.

34. A method of treating non-insulin dependent diabetes mellitus or diabetic syndrome, comprising administering to a patient in need thereof at least one compound of the formula 1 as claimed in claim 5.

35. A method of treating non-insulin dependent diabetes mellitus or diabetic syndrome, comprising administering to a patient in need thereof at least one compound of the formula 1 as claimed in claim 6.

36. A method of treating non-insulin dependent diabetes mellitus or diabetic syndrome, comprising administering to a patient in need thereof at least one compound of the formula 1 as claimed in claim 7.

37. A method of treating non-insulin dependent diabetes mellitus or diabetic syndrome, comprising administering to a patient in need thereof at least one compound of the formula 1 as claimed in claim 8.

38. A method of treating non-insulin dependent diabetes mellitus or diabetic syndrome, comprising administering to a patient in need thereof at least one compound of the formula 1 as claimed in claim 9.

39. A method of treating non-insulin dependent diabetes mellitus or diabetic syndrome, comprising administering to a patient in need thereof at least one compound of the formula 1 as claimed in claim 10.

40. A method of treating non-insulin dependent diabetes mellitus or diabetic syndrome, comprising administering to a patient in need thereof at least one compound of the formula 1 as claimed in claim 11.

41. A method of treating non-insulin dependent diabetes mellitus or diabetic syndrome, comprising administering to a patient in need thereof at least one compound of the formula 1 as claimed in claim 12.

* * * * *

UNITED STATES PATENT AND TRADEMARK OFFICE
CERTIFICATE OF CORRECTION

PATENT NO. : 6,369,088 B2
DATED : April 9, 2002
INVENTOR(S) : Schoenafinger et al.

It is certified that error appears in the above-identified patent and that said Letters Patent is hereby corrected as shown below:

Title page,
Item [57], ABSTRACT,
Line 22, "proceses" should read -- processes --.

Column 21,
Line 41, "$C_1$–$Ci_2$-alkyl," should read -- $C_1$–$C_{12}$-alkyl, --.
Line 65, "cya no," should read -- cyano, --.

Column 22,
Line 10, after "$NR^6$-A-$R^7$", insert a comma.
Line 13, "$R^7$ $C_1$–$C_{18}$-alkyl," should read -- $R^7$ = $C_1$–$C_{18}$-alkyl, --.
Line 53, "$NR^6$-A-R," should read -- $NR^6$-A-$R^7$, --.

Column 23,
Line 14, "Het-(CH2)r–," should read -- Het-$(CH_2)_r$–, --.

Signed and Sealed this

Third Day of December, 2002

JAMES E. ROGAN
*Director of the United States Patent and Trademark Office*